US006672312B2

(12) United States Patent
Acker

(10) Patent No.: US 6,672,312 B2
(45) Date of Patent: Jan. 6, 2004

(54) PULMONARY VEIN ABLATION WITH MYOCARDIAL TISSUE LOCATING

(75) Inventor: David E. Acker, Setauket, NY (US)

(73) Assignee: Transurgical, Inc., Setauket, NY (US)

(*) Notice: Subject to any disclaimer, the term of this patent is extended or adjusted under 35 U.S.C. 154(b) by 20 days.

(21) Appl. No.: 10/062,693

(22) Filed: Jan. 31, 2002

(65) Prior Publication Data

US 2002/0115990 A1 Aug. 22, 2002

Related U.S. Application Data

(60) Provisional application No. 60/265,480, filed on Jan. 31, 2001.

(51) Int. Cl.[7] .............................................. A61B 19/00
(52) U.S. Cl. .......................... 128/898; 606/41; 607/122
(58) Field of Search ..................... 606/41, 42; 607/101, 607/102, 122; 128/898

(56) References Cited

U.S. PATENT DOCUMENTS

| 6,161,543 A | * | 12/2000 | Cox et al. ................... 128/898 |
| 6,237,605 B1 | * | 5/2001 | Vaska et al. ................ 128/898 |
| 6,547,788 B1 | * | 4/2003 | Maguire et al. .............. 606/41 |
| 2002/0165535 A1 | * | 11/2002 | Lesh et al. .................... 606/41 |

* cited by examiner

Primary Examiner—Michael Peffley
(74) Attorney, Agent, or Firm—Lerner, David, Littenberg, Krumholz & Mentlik, LLP

(57) ABSTRACT

A method of treating cardiac arrhythmias by ablating a portion of the myocardial fibers within a pulmonary vein. Myocardial fibers within a pulmonary vein are located and ablated to block conduction of electrical signals to the heart from ectopic foci within the pulmonary vein. The myocardial fibers are located and selectively ablated so as to avoid having to create a circumferential conduction block around the pulmonary vein or ostium. Devices for locating the myocardial fibers, selectively ablating such fibers, and directing ablative energy, are also disclosed.

3 Claims, 4 Drawing Sheets

PULMONARY VEIN ABLATION WITH MYOCARDIAL TISSUE LOCATING

CROSS REFERENCE TO RELATED APPLICATIONS

The present application claims the benefit of U.S. Provisional Application No. 60/265,480, filed Jan. 31, 2001, entitled "PULMONARY VEIN ABLATION WITH MYOCARDIAL TISSUE LOCATING," the disclosure of which is hereby incorporated by reference.

BACKGROUND OF THE INVENTION

The present invention relates to the treatment of cardiac arrhythmias such as atrial fibrillation.

The normal contractions of the heart muscle arrives from electrical impulses generated at a focus within the heart and transmitted through the heart muscle tissue or "myocardial" tissue. This tissue includes fibers which can carry electrical signals. The tissue of the pulmonary vein normally merges with the myocardial tissue of the heart wall at a border near the opening or ostium of the pulmonary vein. In some individuals, fibers of myocardial tissue extend from the wall of the left atrium, through the ostium and along the wall of the pulmonary vein. In some individuals, elongated strands of myocardial tissue extend within the wall of pulmonary vein away from the heart (distally), so that the strains of myocardial tissue project beyond the normal border.

It has been recognized that atrial fibrillation can be caused by an abnormal electrical focus in such strands of myocardial tissue within the pulmonary vein. Because these strains of myocardial tissue merge with myocardial tissue of the heart wall, electrical signals from such an abnormal focus can propagate proximately along one or more strands of myocardial tissue through the myocardial tissue and into the heart wall itself, resulting in abnormal contractions.

It has been recognized that this condition can be treated by locating the abnormal focus of an electrical signal and ablating (i.e., killing or damaging), the tissue at the focus so that the tissue at the focus is replaced by electrically inert scar tissue. However, the focus normally can be found only by a process of mapping the electrophysiological potentials within the heart and in the myocardial fibers of the pulmonary vein. There are significant practical difficulties in mapping the electrical potentials. Moreover, the abnormal potentials which cause atrial fibrillation often are intermittent. Thus, the physician must attempt to map the abnormal potentials while the patient is experiencing an episode of atrial fibrillation.

Another approach that has been employed is to ablate the tissue of the heart wall, so as to form a continuous loop of electrically inert scar tissue extending entirely around the region of the heart wall which contains the ostium of the pulmonary veins. In this approach, the scar tissue prevents the abnormal electrical impulses from propagating into the remainder of the atrial wall. In a variant of this approach, a similar loop-like scar can be formed around the ostium of a single pulmonary vein or in the wall of the pulmonary vein itself proximal to the focus so as to block propagation of the abnormal electrical impulses. Such scar tissue can be created by forming a surgical incision; by applying energies such as radio frequency energy, electrical energy, heat, cold, intense light such as laser light; or ultrasonic energy. Chemical ablation agents also can be employed. Techniques which seek to form a loop like lesion to form a complete conduction block between the focus and the major portion of the myocardial tissue are referred to herein as "loop blocking techniques."

Loop blocking techniques are advantageous because they do not require electrophysiological mapping sufficient to locate the exact focus. However, if a complete loop is not formed, the procedure can fail. Moreover, ablating complete, closed loops without appreciable gaps presents certain difficulties. Thus, some attempts to form a complete loop of ablated tissue around the entire circumference of the pulmonary vein have left significant unablated regions and thus have not formed a complete conduction block. Other attempts have resulted in burning or scaring of adjacent tissues such as nerves. Moreover, attempts to form the required scar tissue using some types of ablation instruments such as radio frequency ablation and unfocused ultrasonic ablation have caused thromboses or stenosis of the pulmonary vein. The potential for these undesirable side effects varies directly with the amount of tissue ablated. In addition, the amount of energy which must be applied in an ablation procedure varies directly with the amount of tissue ablated, an the more energy that need to be applied, the larger the ablation element typically needs to be. Particularly where an ablation element must be introduced into the heart through a catheter, the size of the ablation element and hence the energy delivery capacity per unit time of the ablation element is limited. While these difficulties can be alleviated or eliminated by the use of focused ultrasonic ablation as taught, for example, in copending, commonly assigned U.S. Provisional Patent Application No. 60/218,641 filed Jul. 13, 2000, now U.S. patent application Ser. No. 09/905,227 "Thermal Treatment Methods and Apparatus With Focused Energy Application"; Ser. No. 09/904,963 "Energy Application With Inflatable Annular Lens"; and Ser. No. 09/904,620 "Ultrasonic Transducers," the disclosure of which are incorporated by reference herein, further alternatives would be desirable.

SUMMARY OF THE INVENTION

One aspect of the present invention provides methods of treating cardiac arrhythmias such as atrial fibrillation which arise from abnormal electrical impulses conducted along strands of myocardial tissue in the wall of a blood vessel. A method according to this aspect of the invention desirably includes the steps of finding the locations of myocardial strands around the circumference of the blood vessel and ablating these strands proximal to the focus. Most preferably, the strands are ablated without ablating a continuous loop. Apparatus are also disclosed that may be used to perform this method.

DETAILED DESCRIPTION

Figure 1:
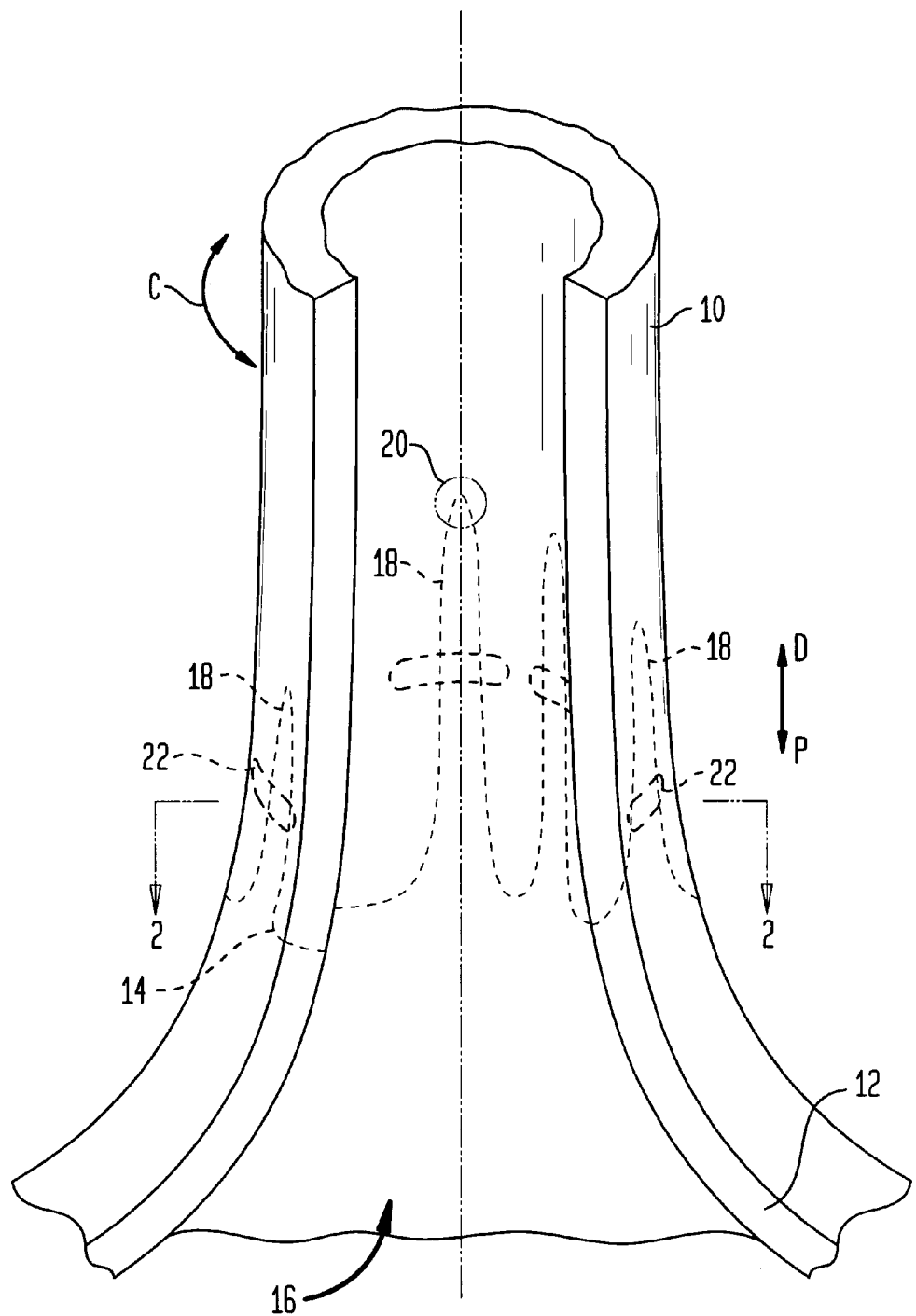
FIG. 1 is a cut-away view of the ostium and a portion of a pulmonary vein.

The method of the invention is used to treat a patient with atrial fibrillation caused by the conduction of abnormal electrical impulses originating from an ectopic foci within the pulmonary vein. As shown in FIG. 1, the pulmonary vein 10 extends distally in direction "D" from the ostium 16 of the heart wall 12. Myocardial fibers 18, normally do not extend past the border 14 between the heart wall and the pulmonary vein. In patients needing treatment with the method of the invention, myocardial fibers 22 extend within the pulmonary vein distally past the border between the pulmonary vein and the heart wall. Ectopic foci 20 within such myocardial fibers propagate proximally in direction "P" from the pulmonary vein into the heart wall 12, causing abnormal contractions, including atrial arrhythmias. In the preferred embodiment, the location of the myocardial fibers is determined through magnetic resonance imaging ("MRI"). In the method of the invention, the myocardial fibers 18 are destroyed by ablating the fibers at a location 22 between the ectopic foci 20 and the heart wall 12. In the preferred method, the fibers are ablated by focused ultrasound.

Figure 2:
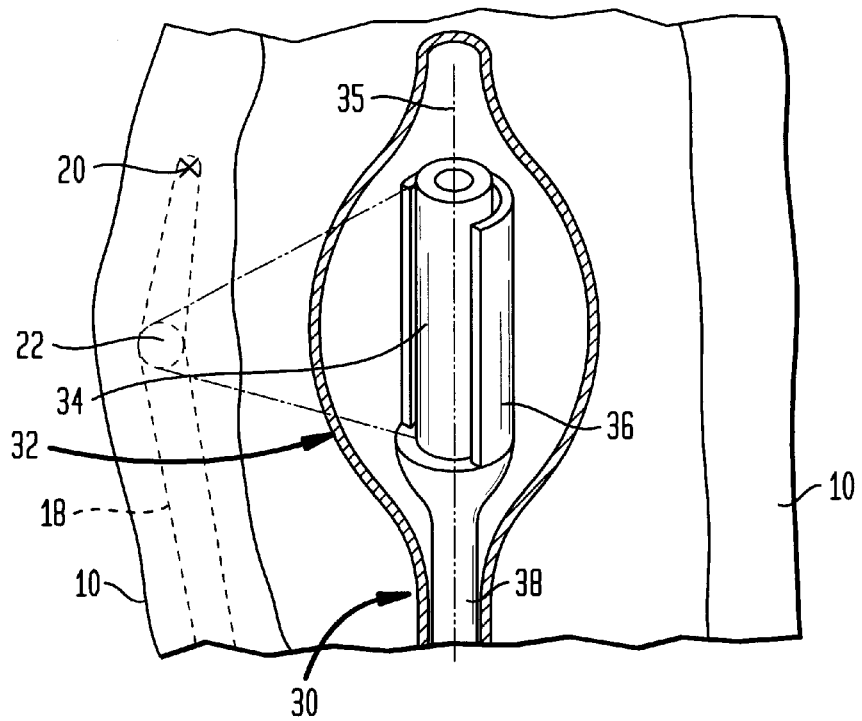
FIG. 2 is a view of the ablation apparatus according to one embodiment of the invention, positioned inside a pulmonary vein.
Figure 3:
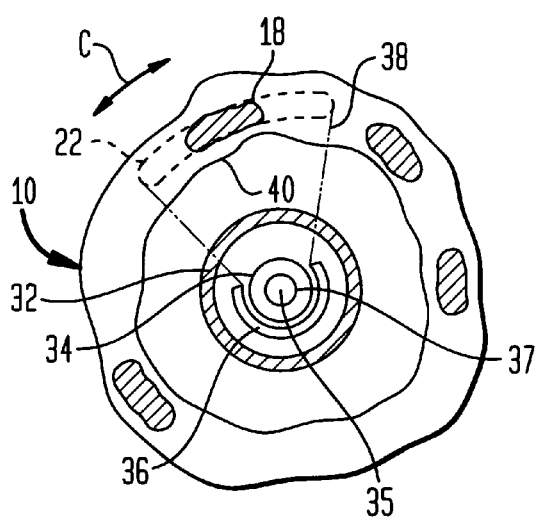
FIG. 3 is a cross-sectional view of the apparatus in FIG. 2.

An ablation device 30 is provided, as shown in FIGS. 2 and 3. Such ablation device includes a catheter 30, having a balloon 32 mounted adjacent to the distal end. In the preferred embodiment, the catheter has a central bore 37 and is inserted into the pulmonary vein 10 by guiding the central bore 37 of the catheter over a wire 35 which has been previously inserted into the pulmonary vein.

For example, as seen in FIG. 1, the vessel wall is ablated in regions 22 along the myocardial fibers 18, the regions being disposed proximal to the focus 20. Each region may encompass an appreciable extent in the circumference direction C, around the central axis of the vein. For example, each region 22 may encompass an arc of 45–135°, typically about 90° around the central axis. This makes alignment between the regions and the myocardial fibers less critical; the ablated region will still interrupt the fiber even if the ablated region is considerably out of its intended circumferential placement. However, the regions 22 desirably do not form a continuous loop around the entire circumference of the vessel. Because the tissue of the blood vessel other than the strands of myocardial tissue does not conduct the electrical impulses, it is possible to form a complete conduction block without forming a complete, closed loop of ablated tissue, provided that all of the myocardial strands are ablated. Therefore, it is not necessary to determine the precise location of the focus 20. Thus, if a complete conduction block is formed by ablating all of the myocardial strands, the focus will be effectively isolated from the heart wall 12 provided that the strands are ablated at a location proximal to the focus.

Ablation of the strands proximal to the focus can be achieved, even without detecting the exact axial location of the focus, by ablating at an axial location as close as practicable to the ostium, i.e., at a location near the ostium but above the main border between the myocardial tissue and the vein wall, where distinct strands of myocardial tissue can be observed.

These strands of myocardial tissue can be observed using magnetic resonance imaging. The ablation procedure can be performed using essentially any device capable of ablating tissue as, for example, electrical, radio frequency, light or the like, but most preferably the ablation procedure is performed using focused ultrasonic energy.

One device for performing such an ablation is depicted in FIGS. 2 and 3. The apparatus includes a catheter 30 having a balloon 32 mounted adjacent the distal end of the catheter. As further described in the U.S. Provisional Patent Application No. 60/218,641 filed Jul. 13, 2000, now U.S. patent application Ser. No. 09/905,227 "Thermal Treatment Methods and Apparatus With Focused Energy Application"; Ser. No. 09/904,963 "Energy Application With Inflatable Annular Lens"; and Ser. No. 09/904,620 "Ultrasonic Transducers," the balloon has a convex shape when inflated. An elongated rod-like ultrasonic transducer 34 is mounted within the balloon with the axis of the transducer extending generally along the proximal to distal axis 35 of catheter 30. An ultrasonically reflecting or ultrasonically absorbing shield 36 is mounted within the balloon and secured to an inner catheter 38, so that the shield may be rotated around the proximal to distal axis 35 of the catheter and transducer by rotating the inner catheter 38 relative to the outer catheter 30.

In operation, the catheter is threaded through the circulatory system into the heart and positioned within the pulmonary vein. Balloon 32 is deflated during the threading process. Conventional techniques used in guiding and threading catheters may be employed as, for example, guide wires, sheaths, and the like (not shown).

Once the catheter is in place within the pulmonary vein 10, balloon 32 is inflated using a liquid having an acoustic impedance close to that of blood, water and tissue, but having an acoustic velocity different from that of blood. As described in greater detail in U.S. Provisional Patent Application No. 60/218,641 filed Jul. 13, 2000, now U.S. patent application Ser. No. 09/905,227 "Thermal Treatment Methods and Apparatus With Focused Energy Application"; Ser. No. 09/904,963 "Energy Application With Inflatable Annular Lens"; and Ser. No. 09/904,620 "Ultrasonic Transducers," the balloon 32 forms an annular lens having a central axis coincident with the central axis 35 of the catheter and transducer. The balloon tends to focus the ultrasonic energy from the entire axial extent of transducer 34 into an axially-narrow zone. Shield 36 limits the circumferential extent of the ultrasonic emission from transducer 34. While the apparatus is in place in the pulmonary vein, with the transducer aligned at the appropriate location along the proximal to distal extent of the vein, the shield 36 is rotated so that the ultrasonic emission zone will be aligned in the circumferential direction C with a myocardial fiber 18.

Shield 36 may be formed from a material such as a polymer or metal having magnetic resonance response substantially different from that of the other materials in the system and from the body tissue, so that the shield 36 can be visualized directly in an MRI image, which image also includes the myocardial strands. Thus, the physician can manually adjust the shield so as to align the emission zone with a strand or strands. Once the emission zone is aligned with a strand, transducer 34 is actuated by applying appropriate ultrasonic frequency driving signals to the transducer through leads (not shown) extending within catheter 30. The ultrasonic energy from the transducer passes out through the wall of balloon 32 and into the surrounding tissue of the vein wall 10 and heats tissue within a region 22 so as to ablate the tissue. The combined effect of the shield (limiting the circumferential extent of ultrasonic emission) and the balloon or lens 32 (focusing the energy into an axially narrow zone) cause the emitted ultrasonic energy to be focused within an axially narrow, arc-like focal region 22. Desirably, this focal region lies within the vein wall, slightly outside of the lumen-defining surface 40 of the vein, so that ablation occurs within the vein wall, with limited or no damage to the lining of the vein wall. This process can be repeated for other strands 18 by turning the shield 36 to redirect the energy from the transducer.

To facilitate high-resolution magnetic resonance imaging of the pulmonary vein and adjacent tissues, the catheter 30 may bear a coil or other antenna for receiving magnetic resonance signals (not shown).

The catheter assembly also may be provided with anchoring and positioning balloons (not shown) proximal and/or distal to the focusing balloon 32 for positioning the focusing balloon coaxially with the vein. In further variants, the focusing balloon 32 may be inflated so that it touches and slightly distends the vein wall, as also disclosed in the U.S. Provisional Patent Application No. 60/218,641 filed Jul. 13, 2000, now U.S. patent application Ser. No. 09/905,227 "Thermal Treatment Methods and Apparatus With Focused Energy Application"; Ser. No. 09/904,963 "Energy Application With Inflatable Annular Lens"; and Ser. No. 09/904,620 "Ultrasonic Transducers."

Figure 4:
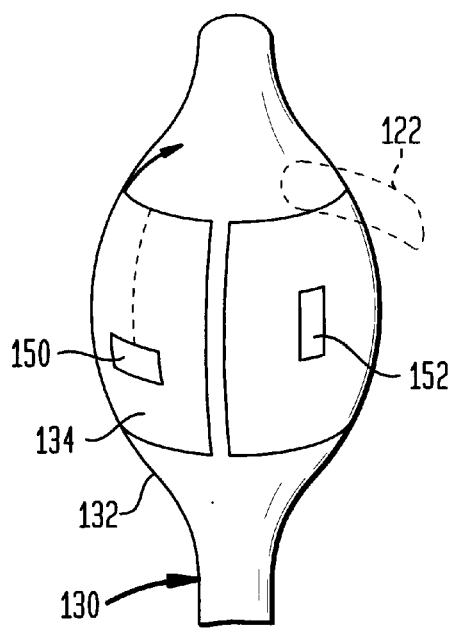
FIG. 4 is a diagrammatic view of the ablation apparatus according to one embodiment of the invention.

Other types of ultrasonic transducers, focusing and registration arrangements can be employed. For example, as shown in FIG. 4, catheter 130 may incorporate a balloon 132 with a curved transducer 134 mounted therein. As disclosed, for example, in copending, commonly assigned U.S. patent application Ser. No. 09/496,988, the disclosure which is hereby incorporated by reference herein, and in the corresponding PCT application PCT/US00/02644, the transducer may be formed from one or more sheets of a polymeric piezoelectric material. The curvature of the transducer is selected so that when the transducer is driven, the transducer tends to focus the emitted energy into the desired arcuate, axially narrow region 122. The transducer may be mounted in a fixed relation to balloon 132 and catheter 130. The balloon, the catheter or both may be provided with markers 150 and 152 which are detectable in an MRI image and which are shaped so that the orientation of the balloon and transducer can be determined by observing images of these markers. In a further variant, the markers are formed from a radio opaque material. The catheter and transducer are positioned and oriented using fluoroscopy. In this regard, it is not essential to visualize both the myocardial strands and the ablation apparatus in a single image. Thus, if an MRI image indicates that the strands are present in a particular sector of the pulmonary vein, the ablation apparatus can be aimed toward that sector using fluoroscopic or other techniques during a subsequent ablation procedure.

Figure 5:
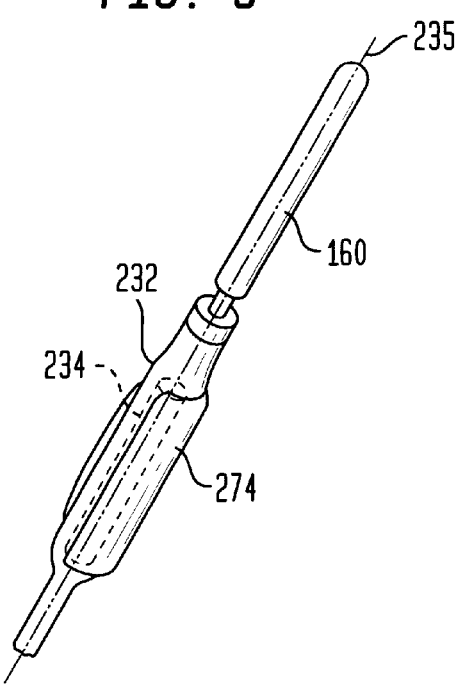
FIG. 5 is a diagrammatic view of the ablation apparatus according to one embodiment of the invention.
Figure 6:
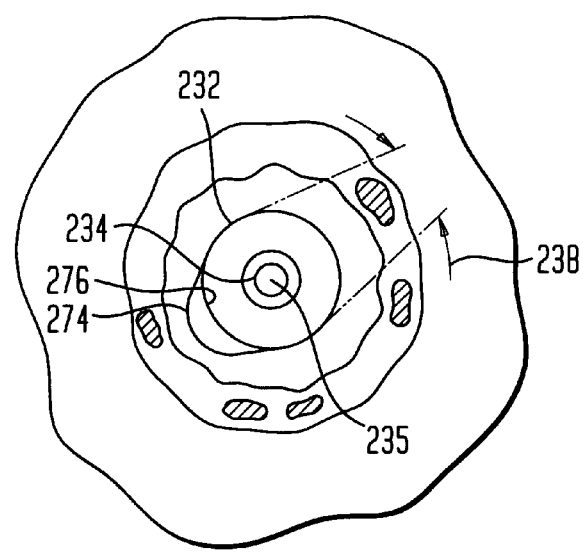
FIG. 6 is a cross-sectional view of the apparatus in FIG. 5.
Figure 7:
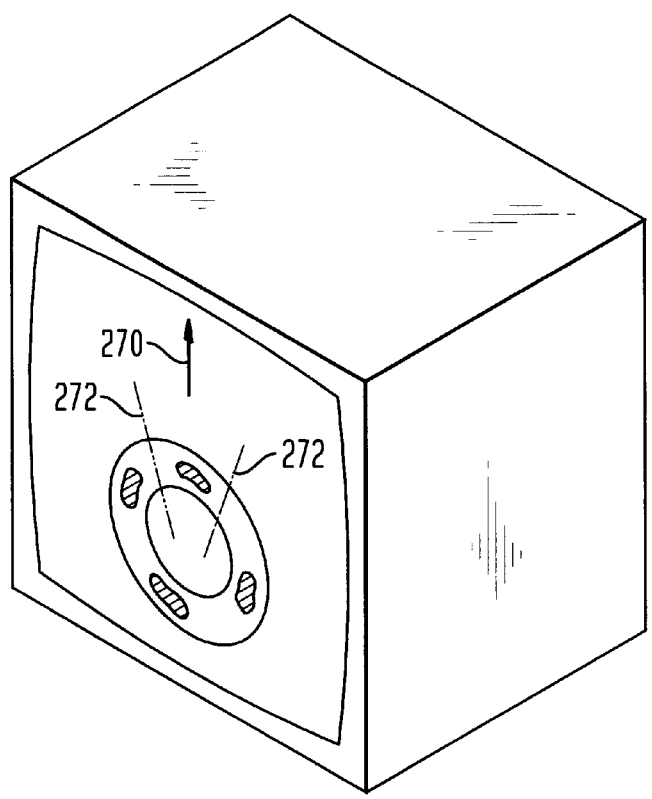
FIG. 7 is a characterization of image displayed on a viewing screen according to the method of one embodiment of the invention.

In a further variant shown in FIG. 5, the catheter carries an intravascular ultrasonic imaging transducer 160 and the pulmonary vein wall and myocardial strands are visualized in an ultrasonic image captured by the intravascular ultrasound transducer. Certain intravascular ultrasound transducers and imaging systems are sold under the trademarks AVANAR and IN-VISION by Jomed USA of Rancho Cordova, Calif., San Diego, Calif. and Conroe, Tex. As shown in FIG. 6, the ablation apparatus is arranged to direct the ultrasonic emission into an arcuate zone 238 having a known relationship to the orientation of transducer 260 around the distal axis 235 of the catheter. For example, the ultrasonic ablation apparatus and associated element may be fixed to the same catheter as the ultrasonic transducer 260. Alternatively, the imaging transducer and ablation apparatus may be mounted on separate catheters which are rotatable relative to one another but which are provided with a transducer (not shown) for monitoring their relative rotational positions. As shown in FIG. 7, provided that the rotational position of the ablation apparatus is known relative to the rotational position of the ultrasonic transducer, an indicium on a view screen or monitor such as an arrow 270 or border lines 272 may be superimposed on the image generated by the ultrasonic transducer so as to indicate the aim of the ablation apparatus.

The particular ablation apparatus depicted in FIGS. 5 and 6 incorporates a dual balloon reflector structure. A balloon 232 encompassing the transducer 234 is inflated with water or other fluid having acoustic impedence close to that of the surrounding blood and tissue, whereas an auxiliary balloon 274 is inflated with air or other fluid having an acoustic impedance different from that of the fluid in balloon 232. As further described in the U.S. Provisional Patent Application No. 60/218,641 filed Jul. 13, 2000, now U.S. patent application Ser. No. 09/905,227 "Thermal Treatment Methods and Apparatus With Focused Energy Application"; Ser. No. 09/904,963 "Energy Application With Inflatable Annular Lens"; and Ser. No. 09/904,620 "Ultrasonic Transducers," the difference in acoustic impedance assures that the interface between the balloons, at wall 276 (FIG. 6) will be highly reflective to ultrasound. The shape of the balloons is selected so that when the balloons are inflated this interface will have a shape appropriate to focus the ultrasound into the desired narrow, arcuate shape.

In further variants, the catheter may be equipped with sensors for detecting magnetic field components or radio frequency signals for determining the position and/or orientation of the ablation apparatus in space. Using known techniques for superimposing an image of a probe onto an MRI or other image of a patient, a representation of the ablation apparatus and/or representation of the aim direction can be superimposed on a magnetic resonance or other image of the patient so that the ablating energy can be aimed. Certain superposition techniques are disclosed in PCT Published International Application WO 95/09562, the disclosure of which is incorporated by reference herein. The various features discussed above can be combined with one another. For example, the shield-based aiming method discussed above with reference to FIGS. 2 and 3 can be employed in conjunction with an intravascular imaging device as discussed with reference to FIGS. 5–7, whereas the dual balloon reflector of FIGS. 5 and 6 can be employed with a direct magnetic resonance imaging aim technique as discussed with reference to FIGS. 2 and 3. In this regard, the gas-filled auxiliary balloon 274 typically will be visible in an MRI image.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating cardiac arrhythmias, comprising: locating myocardial fibers within a pulmonary vein; and ablating regions of said pulmonary vein containing said myocardial fibers so as to prevent conduction of electrical signals by said myocardial fibers, said ablated region being less than one half the circumference of said pulmonary vein.

2. The method of treating cardiac arrhythmias in accordance with claim 1, wherein said myocardial fibers are located using an imaging technique.

3. The method or treating cardiac arrhythmias in accordance with claim 2, wherein the imaging technique is magnetic resonance imaging ("MRI").

* * * * *

UNITED STATES PATENT AND TRADEMARK OFFICE
CERTIFICATE OF CORRECTION

PATENT NO. : 6,672,312 B2
DATED : January 6, 2004
INVENTOR(S) : David E. Acker

It is certified that error appears in the above-identified patent and that said Letters Patent is hereby corrected as shown below:

Column 1,
Line 25, before "pulmonary" insert -- the --.
Line 64, "loop like" should read -- loop-like --.

Column 2,
Line 19, "an" should read -- and --.
Line 19, "need" should read -- needs --.

Column 5,
Line 24, after "disclosure" insert -- of --.

Column 6,
Line 62, "or" should read -- of --.

Signed and Sealed this

Thirteenth Day of April, 2004

JON W. DUDAS
*Acting Director of the United States Patent and Trademark Office*